(12) United States Patent  (10) Patent No.: US 6,870,045 B2
Yang et al.  (45) Date of Patent: Mar. 22, 2005

(54) KITS FOR DETECTING HIV-2

(75) Inventors: Yeasing Y. Yang, San Diego, CA (US); Terrie A. Burrell, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 264 days.

(21) Appl. No.: 10/001,407

(22) Filed: Oct. 22, 2001

(65) Prior Publication Data

US 2002/0177127 A1 Nov. 28, 2002

Related U.S. Application Data

(60) Provisional application No. 60/242,620, filed on Oct. 23, 2000, and provisional application No. 60/280,058, filed on Mar. 30, 2001.

(51) Int. Cl.[7] .............................................. C07H 21/04

(52) U.S. Cl. ................ 536/24.3; 536/23.72; 424/188.1; 424/208.1

(58) Field of Search ............................ 536/24.3, 23.72; 424/188.1

(56) References Cited

U.S. PATENT DOCUMENTS

| | | |
|---|---|---|
| 4,868,105 A | 9/1989 | Urdea et al. |
| 4,965,188 A | 10/1990 | Mullis et al. |
| 5,008,182 A | 4/1991 | Sninsky et al. |
| 5,066,782 A | 11/1991 | Montagnier et al. |
| 5,124,246 A | 6/1992 | Urdea et al. |
| 5,130,238 A | 7/1992 | Malek et al. |
| 5,176,995 A | 1/1993 | Sninsky et al. |
| 5,223,423 A | 6/1993 | Franchini et al. |
| 5,283,174 A | 2/1994 | Arnold, Jr. et al. |
| 5,310,651 A | 5/1994 | Alizon et al. |
| 5,399,491 A | 3/1995 | Kacian et al. |
| 5,437,990 A | 8/1995 | Burg et al. |
| 5,455,166 A | 10/1995 | Walker |
| 5,470,572 A | 11/1995 | Kraiselburd |
| 5,472,840 A | 12/1995 | Stefano |
| 5,545,726 A | 8/1996 | Alizon et al. |
| 5,554,516 A | 9/1996 | Kacian et al. |
| 5,591,578 A | 1/1997 | Meade et al. |
| 5,639,604 A | 6/1997 | Arnold, Jr. et al. |
| 5,656,207 A | 8/1997 | Woodhead et al. |
| 5,658,737 A * | 8/1997 | Nelson et al. .................. 435/6 |
| 5,688,637 A | 11/1997 | Moncany et al. |
| 5,712,385 A | 1/1998 | McDonough et al. |
| 5,770,369 A | 6/1998 | Meade et al. |
| 5,786,208 A | 7/1998 | Clark et al. |
| 5,827,935 A | 10/1998 | Rossi et al. |

(List continued on next page.)

FOREIGN PATENT DOCUMENTS

| | | |
|---|---|---|
| EP | 0403333 B1 | 12/1990 |
| EP | 0404625 B1 | 12/1990 |
| EP | 0525882 A1 | 2/1993 |

(List continued on next page.)

OTHER PUBLICATIONS

Pieniazek, D., et al., 1991, "Identification of mixed HIV–1/HIV–2 Infections in Brazil by polymerase chain reaction", AIDS 5:1293–1299.*

Myers, G., et al., eds., 1993, "Human retroviruses and AIDS : 1993, I–II", Los Alamos National Laboratory, Los Alamos, New Mexico, pp. I–B–1–I–B–9.*

Berkhout et al., "Secondary Structure of the HIV–2 Leader RNA Comprising the tRNA–Primer Binding Site", Nucleic Acids Res., Mar. 1993, 21(5):1171–1178.

(List continued on next page.)

*Primary Examiner*—Jeffrey S. Parkin
(74) *Attorney, Agent, or Firm*—Michael J. Gilly

(57) ABSTRACT

Compositions and methods for synthesizing and detecting HIV-2 specific amplicons. Particularly described are oligonucleotides that are useful as hybridization probes, and amplification primers that facilitate detection of very low levels of HIV-2 nucleic acids.

31 Claims, 1 Drawing Sheet

U.S. PATENT DOCUMENTS

| | | | |
|---|---|---|---|
| 5,840,488 A | | 11/1998 | Hogan |
| 5,840,873 A | | 11/1998 | Nelson et al. |
| 5,843,654 A | | 12/1998 | Heisler et al. |
| 5,843,669 A | | 12/1998 | Kaiser et al. |
| 5,856,088 A | | 1/1999 | McDonough et al. |
| 5,962,665 A | | 10/1999 | Kroeger et al. |
| 5,976,814 A | | 11/1999 | Bard et al. |
| 5,998,172 A | | 12/1999 | Haynes et al. |
| 6,001,558 A | | 12/1999 | Backus et al. |
| 6,020,123 A | | 2/2000 | Sonigo et al. |
| 6,060,245 A | * | 5/2000 | Sorge et al. .................. 435/6 |
| 6,096,321 A | | 8/2000 | Girardeau et al. |

FOREIGN PATENT DOCUMENTS

| | | |
|---|---|---|
| EP | 0655501 A1 | 5/1995 |
| EP | 0750041 A2 | 12/1996 |
| EP | 0239425 A1 | 9/1997 |
| EP | 0806484 A2 | 11/1997 |
| EP | 0887427 A2 | 12/1998 |
| EP | 1026263 A2 | 8/2000 |
| GB | 0125466 A1 | 4/2001 |
| GB | 0162965 A2 | 8/2001 |
| WO | WO 8801302 A1 | 2/1988 |
| WO | WO 8810315 A1 | 12/1988 |
| WO | WO 9322461 A1 | 11/1993 |
| WO | WO 9403472 A1 | 2/1994 |
| WO | WO 9414967 A2 | 7/1994 |
| WO | WO 9503430 A1 | 2/1995 |
| WO | WO 9532305 A1 | 11/1995 |
| WO | WO 9850583 A1 | 11/1998 |
| WO | WO 9855640 A1 | 12/1998 |
| WO | WO 0001850 A2 | 1/2000 |
| WO | WO 0125419 A1 | 4/2001 |

OTHER PUBLICATIONS

Berkhout et al., DATABASE GSN, Online!, Jun. 1993, retrieved from EBI Database accession No. X72325.

Bush et al., "Detection of Human Immunodeficiency Virus Type 1 RNA In Plasma Samples from High–Risk Pediatric Patients Patients by Using the Self–Sustained Sequence Replication Reaction", J Clin Microbiol., Feb. 1992, 30(2):281–286.

De Baar et al., "Design and Evaluation of a Human Immunodeficiency Virus Type 1 RNA Assay Using Nucleic Acid Sequence–Based Amplification Technology Able to Quantify Both Groups M and O Viruses by Using the Long Terminal Repeats as Target" J Clin Microbiol., Jun. 1999, 37(6):1813–1818.

Eiken Chem Co Ltd., Database GSN, Online!, Jul. 1998, retrieved from EBI Database accession No. AAV19509.

Kraiselburd, Database GSN, Online!, Jun. 1996, retrieved from EBI Database accession No. AAT06604.

Pieniazek et al., "Identification of Mixed HIV–1/HIV–2 Infections In Brazil by Polymerase Chain Reaction", AIDS, Nov. 1991, 5(11):1293–1299.

Van Gemen et al., "The One–Tube Quantitative HIV–1 RNA NASBA: Precision, Accuracy, and Application", PCR Methods Appl., Feb. 1995, 4(4):S177–S184.

Abravaya et al., "Performance of a Multiplex Quantitative PCR LCx Assay for Detection of Human Immunodeficiency Virus Type 1 (HIV–1) Group M Subtypes, Group O, and HIV–2", J. Clin. Microbiol., Feb. 2000, 38(2):716–23, American Society for Microbiology, US.

Diamond et al., "Highly Sensitive Method for Amplification of Human Immunodeficiency Virus Type 2 DNA", J. Clin. Microbiol., Mar. 1998, 36(3):809–811, American Society for Microbiology, US.

Reeves et al., "Primary Human Immunodeficiency Virus Type 2 (HIV–2) Isolates Infect CD4–Negative Cells via CCR5 and CXCR4: Comparison with HIV–1 and Simlan Immunodeficiency Virus and Relevance to Cell Tropism In Vivo", J. Virol., Sep. 1999, 73(9):7795–804, American Society for Microbiology, US.

Walther–Jallow et al., "High Concordance between Polymerase Chain Reaction and Antibody Testing of Specimens from Individuals Dually Infected with HIV Types 1 and 2 in Guinea–Bissau, West Africa", AIDS Res. Hum. Retroviruses, Jul. 1999, 15(11):957–62, Mary Ann Liebert Incorporated, US.

* cited by examiner

KITS FOR DETECTING HIV-2

RELATED APPLICATIONS

This application claims the benefit of U.S. Provisional Application Ser. No. 60/242,620, filed Oct. 23, 2000, and U.S. Provisional Application Ser. No. 60/280,058, filed Mar. 30, 2001. The disclosures of these related applications are hereby incorporated by reference.

FIELD OF THE INVENTION

The present invention relates to the field of biotechnology. More specifically, the invention relates to diagnostic assays for detecting HIV-2 nucleic acid sequences.

BACKGROUND OF THE INVENTION

Although the HIV/AIDS pandemic is principally due to infection by HIV-1, a different retrovirus has emerged as another cause of AIDS. This so-called "HIV-2" virus was first isolated from AIDS patients in West Africa in 1986, and was subsequently detected as an infectious agent for the first time in the United States the following year. Fewer than 100 cases of HIV-2 had been reported in the United States through the end of 1994. Despite this seemingly low number, HIV-2 is being identified as the etiologic agent in growing numbers of immunosuppressive diseases that are clinically indistinguishable from AIDS cases that result from HIV-1 infection (Kanki et al., *Science* 232:238 (1986); Kanki et al., *Science* 236:827 (1987); Clavel et al., *Science* 233:343 (1986); Clavel et al., *N. Engl. J. Med.* 316:1180 (1987)). Although HIV-2 is related to HIV-1 by its morphology and tropism for CD4+ cells, it clearly is a distinct virus and not merely an envelope variant of HIV-1.

Indeed, since HIV-2 is only distantly related to HIV-1, with approximately 50% amino acid conservation in the gag and pol proteins and less than 30% conservation in the env gene products, its presence is not effectively detected by serologic assays used for detecting HIV-1 infection (Constantine NT, *AIDS* 7:1 (1993); Markovitz D M, *Ann. Intern. Med.* 118:211 (1993)). As a result, attempts have been made to develop nucleic acid probes that can be used for specifically detecting HIV-2 viral nucleic acids.

Interestingly, the genomes of both HIV-1 and HIV-2 show substantial sequence heterogeneity among different isolates. As a consequence of this heterogeneity, it has been impossible to find substantial regions of absolute sequence conservation between all isolates of HIV-1 or all isolates of HIV-2 (see published European Patent Application EP 0 887 427). Indeed, numerous viral isolates with unique polynucleotide sequences have been identified for each of these viruses, a factor that further complicates the construction of probes for reliable and effective nucleic acid testing.

Since, like HIV-1, HIV-2 also is transmissible through exchange of body fluids, including blood and plasma, it is important to be able to detect infected body fluids before antibodies to the virus are detectable or symptoms are evident in an infected individual. For protection of patients who might otherwise receive an HIV-2-infected body fluid (e.g., whole blood or plasma during transfusion), or products derived from donated blood or plasma, it is particularly important to detect the presence of the virus in the donated body fluid to prevent its use in such procedures or products. It is also important that procedures and reagents used for detecting HIV-2 can detect relatively low numbers of viral copies which may be present in an infected individual, who may be a donor, during the early stages of infection.

Assays and reagents for detecting HIV-2 have been previously disclosed in, for example, U.S. Pat. Nos. 6,020,123, 5,688,637, 5,545,726 and 5,310,651; European Patent Nos. EP 0404625 B1 and EP 0239425 B1 and published European Patent Application Nos. EP 1026236 A2, EP 0887427 A2.

SUMMARY OF THE INVENTION

A first aspect of the invention relates to a composition for detecting an HIV-2 nucleic acid sequence. The composition includes a first amplification oligonucleotide having a length of up to 100 nucleotides. This first amplification oligonucleotide includes a sequence of 9–34 contiguous bases contained within the sequence of SEQ ID NO:9. Also included in the composition is a second amplification oligonucleotide having a length of up to 100 nucleotides. This second amplification oligonucleotide includes a sequence of 19–40 contiguous bases from the sequence of SEQ ID NO:1. In a preferred embodiment of the invention, the length of the second amplification oligonucleotide is 19–40 nucleotides. In an even more preferred embodiment of the invention, the length of the first amplification oligonucleotide is 18–60 nucleotides, more preferably 18–34 nucleotides, and still more preferably 18–25 nucleotides. Examples of first amplification oligonucleotides having lengths in the range of 18–25 nucleotides are given by SEQ ID NO:10, SEQ ID NO:11, SEQ ID NO:12, SEQ ID NO:13 and SEQ ID NO:14. In another preferred embodiment, when the length of the second amplification oligonucleotide is in the range of 19–40 nucleotides, the length of the first amplification oligonucleotide is in the range of 18–60 nucleotides and includes a promoter sequence.

According to another preferred embodiment of the invention, when the first amplification oligonucleotide has a length of up to 100 nucleotides, the length of the second amplification oligonucleotide is in the range of 19–21 nucleotides. In another preferred embodiment, the first amplification oligonucleotide has a length of 18–34 nucleotides, and the second amplification oligonucleotide has a length of 19–21 nucleotides. In still another preferred embodiment, when the first amplification oligonucleotide has a length of 18–60 nucleotides the second amplification oligonucleotide has a length of 19–21 nucleotides. In yet another preferred embodiment of the invention, when the first amplification oligonucleotide has a length of 18–60 nucleotides, and the second amplification oligonucleotide has a length of 19–40 nucleotides, the first amplification oligonucleotide is a promoter-primer having the sequence of any one of SEQ ID NOs:15–19. In still yet another preferred embodiment of the invention, when the first amplification oligonucleotide has a length of 18–60 nucleotides, and the second amplification oligonucleotide has a length of 19–21 nucleotides, the second amplification oligonucleotide can have the sequence of any one of SEQ ID NOs:2–7. In still yet another preferred embodiment of the invention, when the first amplification oligonucleotide has a length of 18–60 nucleotides, and the second amplification oligonucleotide has a length of 19–21 nucleotides, the first amplification oligonucleotide can further include a promoter sequence. For example, the first amplification oligonucleotide can be a promoter-primer having the sequence of any one of SEQ ID NOs:15–19. Alternatively, when the first amplification oligonucleotide has a length of 18–60 nucleotides, when the second amplification oligonucleotide has a length of 19–21 nucleotides, and when the first amplification oligonucleotide further includes a promoter sequence, the sequence of the second amplification oligonucleotide can be any one of SEQ ID NOs:2–7. In still yet another preferred embodiment of the invention, when the first amplification oligonucleotide has a length of 18–60 nucleotides, when the second amplification oligonucleotide has a length of 19–21 nucleotides, and when the first amplification oligonucleotide is a promoter-primer having the sequence of any one of SEQ ID NOs:15–19, the second amplification oligonucleotide can have a sequence given by any one of SEQ ID NOs:2–7. According to another preferred embodiment of the invention, the length of the first amplification oligonucleotide is 18–25 nucleotides, and the length of the second amplification oligonucleotide is 19–21 nucleotides. When this is the case, the first amplification oligonucleotide can have a sequence, for example, that is any one of SEQ ID NOs:10–14. Alternatively, when the length of the first amplification oligonucleotide is 18–25 nucleotides, and the length of the second amplification oligonucleotide is 19–21 nucleotides, the second amplification oligonucleotide can have a sequence given by any one of SEQ ID NOs:2–7. In still yet another highly preferred embodiment of the invention, when the length of the first amplification oligonucleotide is 18–25 nucleotides and the length of the second amplification oligonucleotide is 19–21 nucleotides, and when the first amplification oligonucleotide has a sequence given by any one of SEQ ID NOs:10–14, the second amplification oligonucleotide can be any one of SEQ ID NOs:2–7. According to another embodiment, the composition which includes the first and second amplification oligonucleotides, each having lengths of up to 100 nucleotides, may further include an oligonucleotide detection probe having a sequence that includes SEQ ID NO:21 or the complement thereof. Preferably, the detection probe has a length of up to 18 nucleotides, and more preferably has the sequence of any one of SEQ ID NOs:22–27. In a highly preferred embodiment the sequence of the first amplification oligonucleotide is any one of SEQ ID NOs:10–19, the sequence of the second amplification oligonucleotide is any one of SEQ ID NOs:2–7, and the sequence of the oligonucleotide detection probe is any one of SEQ ID NOs:22–27.

A second aspect of the invention relates to a method for determining whether a biological sample containing nucleic acids includes an HIV-2 nucleotide base sequence. A first step of the invented method involves contacting the nucleic acids of the biological sample with a composition that includes a first amplification oligonucleotide that includes the sequence of SEQ ID NO:9 and has a length of up to 100 nucleotides. This first amplification oligonucleotide has a sequence of 9–34 contiguous bases contained within the sequence of SEQ ID NO:9. The composition further includes a second amplification oligonucleotide having 19–40 contiguous bases from the sequence of SEQ ID NO:1 and a length of up to 100 nucleotides. A second step involves amplifying any of the HIV-2 nucleotide base sequence present in the biological sample to produce amplified nucleic acids. Finally, there is a step for detecting the amplified nucleic acids produced in the amplifying step. According to the invented method, positive detection of the amplified nucleic acids indicates that the biological sample included the HIV-2 nucleotide base sequence. In a preferred embodiment, the first amplification oligonucleotide is 18–60 nucleotides long and the second amplification oligonucleotide is 19–40 nucleotides long. In an even more preferred embodiment that employs the same two oligonucleotides, the first amplification oligonucleotide is a promoter-primer, and the amplifying step involves amplifying by the Transcription Mediated Amplification reaction, or "TMA." According to a different preferred embodiment of the invention, when the first and second amplification oligonucleotides have lengths of 18–60 and 19–40 nucleotides, respectively, the detecting step involves first hybridizing the amplified nucleic acids with a hybridization assay probe that is specific for the amplified nucleic acids, and thereafter measuring the amount of the hybridization assay probe that hybridized to the amplified nucleic acids. This can be accomplished, for example, by using a labeled nucleic acid probe. In an alternative procedure, the hybridization assay probe includes the sequence of SEQ ID NO:21 or the complement thereof, and has a length of up to 35, or up to 22 nucleotides.

A third aspect of the invention relates to an oligonucleotide having a length of up to 35 nucleotides, and having the sequence of SEQ ID NO:21 or the complement thereof. In certain preferred embodiments the labeled oligonucleotide has a length of up to 22 nucleotides. Preferably, the oligonucleotide has at least 16 contiguous nucleotides contained within the sequence of SEQ ID NO:20 or the complement thereof. In one embodiment the oligonucleotide has the sequence of SEQ ID NO:20 or the complement thereof. In another preferred embodiment, the oligonucleotide that includes the sequence of SEQ ID NO:21 or the complement thereof has a length of up to 18 nucleotides. For example, the oligonucleotide can have the sequence of any one of SEQ ID NO:22 or the complement thereof, SEQ ID NO:23 or the complement thereof, SEQ ID NO:24 or the complement thereof, SEQ ID NO:25 or the complement thereof, SEQ ID NO:26 or the complement thereof, and SEQ ID NO:27 or the complement thereof. Certain labeled oligonucleotides have lengths of exactly 18 nucleotides. In other embodiments of the invention, wherein the oligonucleotide has a length of up to 22 nucleotides and includes the sequence of SEQ ID NO:21 or the complement thereof, the oligonucleotide can be DNA, but alternatively can include at least one nucleotide analog. Preferably, the nucleotide analog has a methoxy group at the 2' position of a ribose moiety. In another preferred embodiment of the invention, the oligonucleotide that includes the sequence of SEQ ID NO:21 or the complement thereof, and that has a length of up to 18 nucleotides, also includes a detectable label. Examples of useful detectable labels include chemiluminescent labels and radiolabels. A particularly preferred example of a chemiluminescent label is an acridinium ester.

A fourth aspect of the invention relates to a method for detecting the presence of HIV-2 nucleic acids in a biological sample. A first step in the invented method involves providing to the biological sample a hybridization probe that is up to 35 nucleotides in length and that includes the sequence of SEQ ID NO:21 or the complement thereof. Next, there is a step for hybridizing under a high stringency condition any HIV-2 nucleic acid that may be present in the biological sample with the hybridization probe to form a probe:target duplex. Finally, there is a step for detecting the probe:target duplex as an indicator of the presence of HIV-2 in the biological sample. In some embodiments of the invented method the length of the hybridization probe provided to the biological sample is only up to 22 nucleotides instead of up to 22 nucleotides. In another preferred embodiment of the invention, the biological sample is a blood product that is either plasma or serum. In a more preferred embodiment, prior to carrying out the "providing" step there is a step for releasing nucleic acid from any HIV-2 that may be present in the biological sample. In an even more highly preferred embodiment of the invention, after conducting the "releasing" step there is an additional step for capturing onto a solid support the nucleic acid released from any HIV-2 that may be present in the biological sample. In another embodiment of the invention, the biological sample used in the method is a lysate. Exemplary high stringency hybridization conditions that can be used for carrying out the invented method include: (1) 0.48 M sodium phosphate buffer, 0.1% sodium dodecyl sulfate, and 1 mM each of EDTA and EGTA; and (2) a salt concentration in the range of 0.6–0.9 M. In still another embodiment, the hybridization probe provided to biological sample in the first step of the invented method has a sequence that can be any one of of SEQ ID NO:22 or the complement thereof SEQ ID NO:23 or the complement thereof, SEQ ID NO:24 or the complement thereof, SEQ ID NO:25 or the complement thereof, SEQ ID NO:26 or the complement thereof, and SEQ ID NO:27 or the complement thereof. In a highly preferred embodiment of the invented method, the hybridization probe includes at least one nucleotide analog. In a more highly preferred embodiment, the hybridization probe also includes a detectable label. For example, the detectable label can be an acridinium ester, and the detecting step can include performing luminometry to detect any of the probe:target duplex that formed during the hybridizing step.

A fifth aspect of the invention relates to a kit for detecting HIV-2 nucleic acids. In general, kits in accordance with the present invention may include any of the above-described compositions in packaged combination. A particular embodiment of the invented kit includes a first amplification oligonucleotide and a second amplification oligonucleotide. The first amplification oligonucleotide includes a sequence of 9–34 contiguous bases contained within the sequence of SEQ ID NO:9, and has a length of up to 100 nucleotides. The second amplification oligonucleotide includes a sequence of 19–40 contiguous bases from the sequence of SEQ ID NO:1, and has a length of up to 100 nucleotides. Preferably the kit also includes an oligonucleotide detection probe that may be employed for detecting HIV-2 amplicons that were synthesized using the first and second amplification oligonucleotides. The detection probe preferably includes the sequence of SEQ ID NO:21 or the complement thereof, and a detectable label. The detection probe may have a length of up to 35 nucleotides. The invented kits may further contain capture oligonucleotides that may be used for purifying HIV-2 template nucleic acids away from other species prior to conducting an amplification. Examples of capture oligonucleotides that may be packaged into kits have the sequences of SEQ ID NO:31 and SEQ ID NO:32.

A sixth aspect of the invention relates to a composition that includes a first oligonucleotide which includes a sequence of 9–34 contiguous bases contained within the sequence of SEQ ID NO:9, and which has a length of up to 100 nucleotides. More preferably, the length of the first oligonucleotide is 18–60 nucleotides. Still more preferably, the length of the first oligonucleotide is 18–34 nucleotides. Yet even more preferably, the length of the first oligonucleotide is 18–25 nucleotides. In certain preferred embodiments wherein the length of the first oligonucleotide is in the range of 18–34 nucleotides, the sequence of the first oligonucleotide can include 18–34 contiguous bases contained within the sequence of SEQ ID NO:9. When this is the case, the sequence of the first oligonucleotide can, in certain highly preferred embodiments of the invention, be any one of SEQ ID NO:10, SEQ ID NO:11, SEQ ID NO:12, SEQ ID NO:13 and SEQ ID NO:14. In other preferred embodiments of the invention, when the first oligonucleotide has a length of up to 100 nucleotides, or a length of 18–60 nucleotides, the sequence of the first oligonucleotide can further include a promoter. In such an instance, the first oligonucleotide may function as a promoter-primer. For example, under this circumstance the sequence of the first oligonucleotide may be any one of SEQ ID NO:15, SEQ ID NO:16, SEQ ID NO:17, SEQ ID NO:18 and SEQ ID NO:19. In accordance with a different embodiment of the invention, when the first oligonucleotide has a length of up to 100 nucleotides, or a length of 18–60 nucleotides, and a sequence that includes 9–34 contiguous bases contained within the sequence of SEQ ID NO:9, there can be further included a second oligonucleotide. This second oligonucleotide may have a length of up to 35 nucleotides, or more preferably up to 22 nucleotides, and a sequence that includes SEQ ID NO:21. In a particular example, the sequence of the second oligonucleotide may include at least 16 contiguous nucleotides contained within the sequence of SEQ ID NO:20. When this is the case, it is highly preferred for the length of the second oligonucleotide to be in the range of 16–18 nucleotides. In some instances, it is desirable for the second oligonucleotide to further include a detectable label. In accordance with still a different embodiment of the invention, when the composition includes a first oligonucleotide having a length of up to 100 nucleotides and a sequence that includes 9–34 contiguous bases contained within the sequence of SEQ ID NO:9, and further includes a second oligonucleotide having a length of up to 22 nucleotides and a sequence that includes SEQ ID NO:21, there is further included a third oligonucleotide having a length of up to 100 nucleotides and a sequence that includes 19–40 contiguous bases from the sequence of SEQ ID NO:1. In a highly preferred version of this embodiment, the length of the third oligonucleotide is 19–40 nucleotides, or even more preferably 19–21 nucleotides. Particular examples of sequences of the third oligonucleotide in accordance with such embodiments of the invention include any one of SEQ ID NO:2, SEQ ID NO:3, SEQ ID NO:4, SEQ ID NO:5, SEQ ID NO:6 and SEQ ID NO:7.

DEFINITIONS

The following terms have the following meanings for the purposes of this disclosure, unless expressly stated to the contrary herein.

As used herein, a "biological sample" is any tissue or polynucleotide-containing material obtained from a human. Biological samples in accordance with the invention include peripheral blood, plasma, serum, bone marrow, biopsy tissue including lymph nodes, respiratory tissue or exudates, gastrointestinal tissue, cervical swab samples, semen or other body fluids, tissues or materials. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence. The term includes polymers containing analogs of naturally occurring nucleotides and particularly includes analogs having a methoxy group at the 2' position of the ribose (OMe). As used herein, methoxy polynucleotides or oligonucleotides containing "T" residues have a methoxy group at the 2' position of the ribose moiety, and a uracil at the base position of the nucleotide. When particularly specified as "OMeT" it is meant that the base position of the nucleotide is occupied by a thymine residue.

As used herein, a "detectable label" is a chemical species that can be detected or can lead to a detectable response.

Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. These labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE, 1- or 3-methyl-meta-difluoro-AE, and 2-methyl-AE). Synthesis and methods of attaching labels to nucleic acids and detecting labels are well known in the art (e.g., see Sambrook et al., Molecular Cloning, A Laboratory Manual, 2nd ed. (Cold Spring Harbor Laboratory Press, Cold Spring Habor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333; and Becker et al., European Patent App. No. 0 747 706).

As used herein, "amplification" refers to an in vitro procedure for obtaining multiple copies of a target nucleic acid sequence, its complement or fragments thereof.

By "target nucleic acid" or "target" is meant a nucleic acid containing a target nucleic acid sequence.

By "target nucleic acid sequence," "target nucleotide sequence," "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are preferred for conducting nucleic acid amplification procedures of the type disclosed herein.

As used herein, a "probe" is a nucleic acid oligonucleotide that hybridizes specifically to a target sequence in a nucleic acid, preferably in an amplified nucleic acid, under conditions that promote hybridization, to form a detectable hybrid. A probe may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and other sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Preferred oligonucleotides of the present invention fall in a size range having a lower limit of about 10 to about 60 residues. Oligonucleotides may be purified from naturally occurring sources, but preferably are synthesized using any of a variety of well known enzymatic or chemical methods.

As used herein, an "amplification primer" or "amplification oligonucleotide" is an oligonucleotide that hybridizes to a target nucleic acid, or its complement, and participates in a nucleic acid amplification reaction. Amplification primers, or more simply "primers," may be an optionally modified oligonucleotide which is capable of hybridizing to a template nucleic acid and which has a 3' end that can be extended by a DNA polymerase activity.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0 to 2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least contiguous bases being compared, which may range from 0 to 2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including a basic "nucleotides"), but in which the entire complementary base sequence is capable of specifically hybridizing with another base sequence in appropriate hybridization conditions. Contiguous bases are preferably at least about 80%, more preferably at least about 90%, and most preferably about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual*, 2$^{nd}$ ed. (Cold Spring Harbor Laboratory Press, Cold Spring Harbor, N.Y., 1989) at §§ 1.90–1.91, 7.37–7.57, 9.47–9.51 and 11.47–11.57 particularly at §§ 9.50–9.51, 11.12–11.13, 11.45–11.47 and 11.55–11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect HIV-2 nucleic acids in biological samples such as whole blood or plasma, at a copy number of about 100 copies of the HIV-2 nucleic acid. Any component(s), composition(s), or method step(s) that have a material effect on the basic and novel characteristics of the present invention would fall outside of this term.

DETAILED DESCRIPTION OF THE INVENTION

Figure 1:
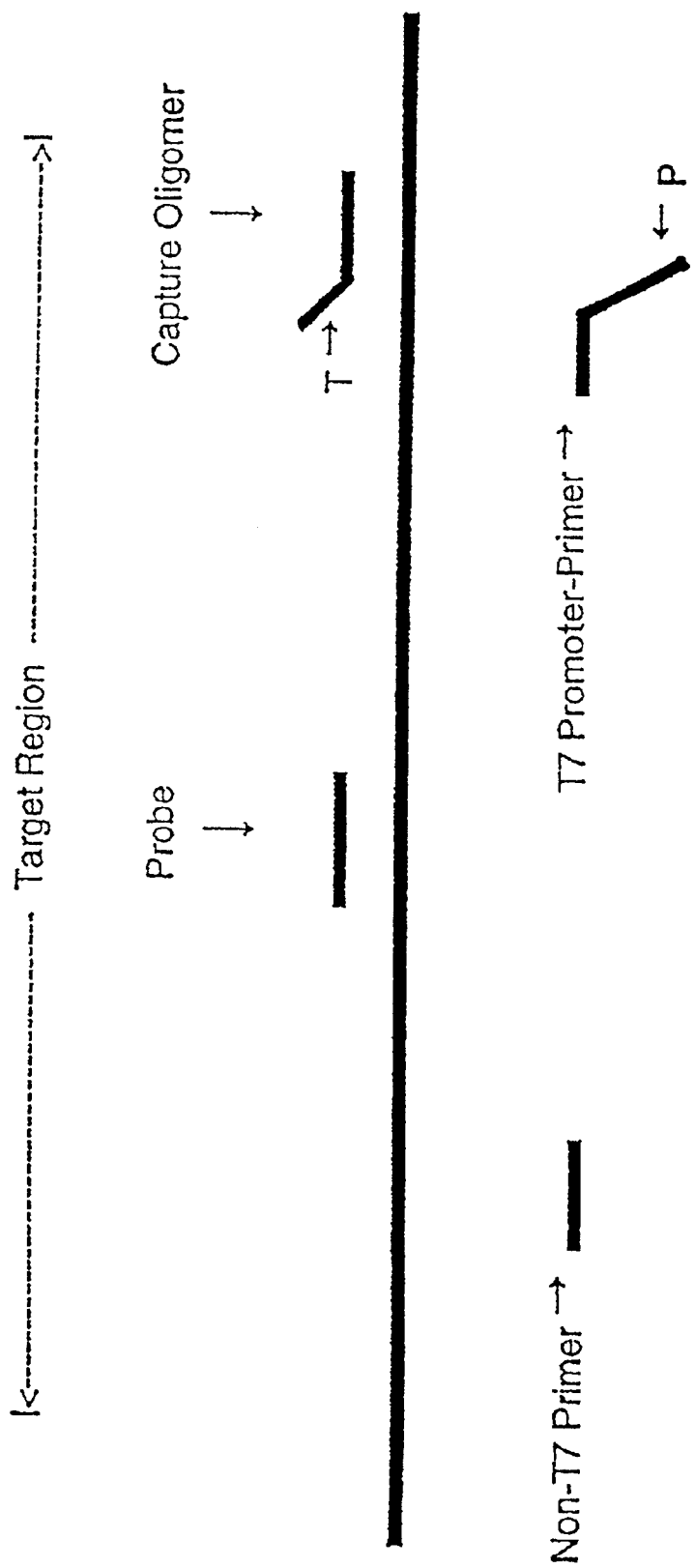
FIG. 1 is a schematic diagram illustrating the various polynucleotides that can be used for detecting a target region within the HIV-2 nucleic acid (represented by a thick horizontal line). Positions of the following nucleic acids are shown relative to the target region: "Capture Oligonucleotide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

The present invention relates to compositions and methods for selectively detecting the nucleic acids of HIV-2. The compositions disclosed herein are useful for amplifying and detecting these nucleic acids in biological samples such as human blood, serum, plasma or other body fluid or tissue to be tested for the presence of viral nucleic acids. The amplification primers disclosed herein advantageously can be used as components of multiplex amplification reactions, wherein several amplicon species can be produced from a complex assortment of primers and accessory polynucleotides. For example, the primers disclosed herein can be used in multiplex amplification reactions that synthesize amplicons corresponding to polynucleotides of unrelated viruses.

The probes, primers and methods disclosed herein can be used either in diagnostic applications or for screening donated blood and blood products or other tissues that may contain infectious particles.

Introduction and Overview

Those having an ordinary level of skill in the art will appreciate that nucleic acid testing represents a convenient and highly sensitive method for detecting virus-specific polynucleotides in biological samples, such as donated blood or plasma. Since individuals newly infected with HIV-1 typically produce detectable levels of antibodies reactive with viral antigens 1–2 months after infection, serologic testing during the first month following exposure to the virus could give a false-negative result and allow samples contaminated with HIV-1 to enter the blood supply with devastating consequences. In the same way that early detection of HIV-1 exposure can help ensure safety of the donated blood supply, early detection of HIV-2 exposure could provide the same benefits. Accordingly, the most sensitive testing procedures for detecting HIV-2 will rely on detection of virus-specific nucleic acids as distinguished from a host's immune response to infection.

The present invention includes compositions (nucleic acid capture oligonucleotides, amplification oligonucleotides and probes) and methods for detecting HIV-2 nucleic acids in a biological sample. To design oligonucleotide sequences appropriate for such uses, known HIV-2 DNA sequences, including subtypes, were first aligned by matching regions having similar sequences and then comparing the sequences to identify candidate regions of the HIV-2 viral genome that could serve as reagents in a diagnostic assay. Based on these comparisons, the LTR region of the HIV-2 genome was selected for detection using the capture oligonucleotides, primers and probes shown schematically in FIG. 1. Portions of sequences containing relatively few sequence variants between the compared sequences were chosen as starting points for designing synthetic oligonucleotides suitable for use in capture, amplification and detection of amplified sequences. Other considerations in designing oligonucleotides included the relative GC content of the sequence (ranging from about 30% to about 55%), and the relative absence of predicted secondary structure (e.g., hairpin turns forming intramolecular hybrids) within a sequence.

Based on these analyses, the capture oligonucleotide, amplification oligonucleotides and probe sequences presented below were designed. Those having an ordinary level of skill in the art will appreciate that primer sequences specific for HIV-2, with or without the T7 promoter sequence, may be used as primers in the various primer-based in vitro amplification methods described below. Additionally, it is also contemplated that the hybridization probes disclosed herein could be used as amplification primers, and that the amplification primers disclosed herein could be used as hybridization probes. The amplification and detection assay detailed below is useful for detecting at least subtypes A, B, C and D of HIV-2. Notably, the portion of the HIV-2 genome that serves as a target for the probes disclosed herein does not find a corresponding sequence in the HIV-1 genome. Thus, the probes are specific for HIV-2 and not HIV-1.

Useful Amplification Methods

Amplification methods useful in connection with the present invention include: Transcription Mediated Amplification (TMA), the Polymerase Chain Reaction (PCR), Nucleic Acid Sequence-Based Amplification (NASBA), Strand Displacement Amplification (SDA), and amplification methods using self-replicating polynucleotide molecules and replication enzymes like MDV-1 RNA and Q-beta enzyme. Methods for carrying out these various amplification techniques respectively can be found in U.S. Pat. No. 5,399,491; U.S. Pat. No. 4,965,188; published European patent application EP 0 525 882, U.S. Pat. No. 5,455,166, U.S. Pat. No. 5,472,840 and Lizardi et al., BioTechnology 6:1197 (1988). U.S. Pat. No. 5,554,516 describes a method of amplifying a target RNA sequence using a single promoter-primer in the absence of a primer that forms a hybrid with the complement of the target RNA sequence. The disclosures of these documents which describe how to perform nucleic acid amplification reactions are hereby incorporated by reference.

In a highly preferred embodiment of the invention, HIV-2 nucleic acid sequences are amplified using a TMA protocol. According to this protocol, the reverse transcriptase which provides the DNA polymerase activity also possesses an endogeneous RNase H activity. One of the primers used in this procedure contains a promoter sequence positioned upstream of a sequence that is complementary to one strand of a target nucleic acid that is to be amplified. In the first step of the amplification, a promoter-primer hybridizes to the HIV-2 target RNA at a defined site. Reverse transcriptase creates a DNA copy of the target RNA by extension from the 3' end of the promoter-primer. The RNA strand in the resulting RNA:DNA duplex is degraded by an RNase H activity which optionally may be an inherent activity of the reverse transcriptase. A second primer then binds to the DNA strand. A second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100–1000 copies of RNA amplicon, this expansion can result in the production of 10 billion amplicons in less than one hour. The entire process is autocatalytic and is performed at a constant temperature.

Methods of detecting HIV-2 amplicons may be as simple as staining a electrophoretically separated nucleic acid amplification products produced using a pair of oligonucleotide primers. As detailed below, preferred detection methods employ HIV-2 specific hybridization probes.

Structural Features of Primers

As indicated above, a "primer" refers to an optionally modified oligonucleotide which is capable of hybridizing to a template nucleic acid and which has a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified, e.g., by the addition of propyne groups, so long as the modified base moiety retains the ability to form a non-covalent association with G, A, C, T or U and an oligonucleotide comprising at least one modified nucleotide base moiety is not sterically prevented from hybridizing with a single-stranded nucleic acid. Common sugar moieties that comprise the primer backbone include ribose and deoxyribose, although 2'-O-methyl ribose (OMe), halogenated sugars, and other modified also may be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). A preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., luminescent/quencher) positioned so that a different signal is produced when the Molecular Torch is self-hybridized as opposed to when the Molecular Torch is hybridized to a target nucleic acid, thereby permitting detection of probe:target duplexes in a test sample in the presence of unhybridized probe having a viable label associated therewith. Molecular Torches are fully described in International Publication No. WO 00/01850, the disclosure of which is hereby incorporated by reference.

Another example of a self-complementary hybridization assay probe is a structure commonly referred to as a "Molecular Beacon." Molecular Beacons comprise nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and a quencher (e.g., DABCYL and EDANS). Molecular Beacons are fully described in U.S. Pat. No. 5,925,517, the disclosure of which is hereby incorporated by reference.

Synthetic techniques and methods of bonding labels to nucleic acids and detecting labels are well known in the art (e.g., see Sambrook et al., *Molecular Cloning, A Laboratory Manual*, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; and Kourilsky et al., U.S. Pat. No. 4,581,333).

Chemical Composition of Probes

Probes in accordance with the invention comprise polynucleotides or polynucleotide analogs and may carry a detectable label covalently bonded thereto. Nucleosides or nucleoside analogs of the probe comprise nitrogenous heterocyclic bases, or base analogs, where the nucleosides are linked together, for example by phospohdiester bonds to form a polynucleotide. Accordingly, a probe may comprise conventional ribonucleic acid (RNA) and deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Int'l Pub. No. WO 95/32305), phosphorothioate linkages, methylphosphonate linkages or combinations thereof. Sugar moieties of the probe may be either ribose or deoxyribose, or similar compounds having known substitutions, such as, for example, 2' methoxy substitutions (OMe) and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5–36, Adams et al., ed., 11$^{th}$ ed., 1992), known derivatives of purine or pyrimidine bases (e.g., N$^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Int'l Pub. No. WO 93/13121) and "a basic" residues where the backbone includes no nitrogenous base for one or more residues of the polymer (see Arnold et al., U.S. Pat. No. 5,585,481). A nucleic acid may comprise only conventional sugars, bases and linkages found in RNA and DNA, or may include both conventional components and substitutions (e.g., conventional bases linked via a methoxy backbone, or a nucleic acid including conventional bases and one or more base analogs).

Selection of Amplification Primers and Detection Probes Specific for HIV-2

Useful guidelines for designing amplification primers and probes with desired characteristics are described herein. The optimal sites for amplifying and probing HIV-2 nucleic acids contain two, and preferably three, conserved regions greater than about 15 bases in length, within about 350 bases, and preferably within 150 bases, of contiguous sequence. The degree of amplification observed with a set of primers or promotor-primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described by Hogan et al., in U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally primarily determine hybrid stability.

Amplification primers and probes should be positioned to minimize the stability of the oligonucleotide:nontarget (i.e., nucleic acid with similar sequence to target nucleic acid) nucleic acid hybrid. It is preferred that the amplification primers and detection probes are able to distinguish between target and non-target sequences. In designing primers and probes, the differences in these Tm values should be as large as possible (e.g., at least 2° C. and preferably 5° C.).

Regions of the nucleic acid which are known to form strong internal structures inhibitory to hybridization are less preferred as primers or probes. Examples of such structures include hairpin loops. Likewise, oligonucleotides with extensive self-complementarity should be avoided.

The degree of non-specific extension (primer-dimer or non-target copying) can also affect amplification efficiency. For this reason, primers are selected to have low self- or cross-complementarity, particularly at the 3' ends of the sequence. Long homopolymer tracts and high GC content are avoided to reduce spurious primer extension. Commercially available computer software is available to aid in this aspect of the design. Available computer programs include MacDNASIS™ 2.0 (Hitachi Software Engineering American Ltd.) and OLIGO® ver. 4.1 (National Bioscience).

Those having an ordinary level of skill in the art will appreciate that hybridization involves the association of two single strands of complementary nucleic acid to form a hydrogen bonded double strand. It is implicit that if one of the two strands is wholly or partially involved in a hybrid that it will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

Rate of polynucleotide hybridization can be measured by determining the $C_0t_{1/2}$. The rate at which a polynucleotide hybridizes to its target is a measure of the thermal stability of the target secondary structure in the target binding region. The standard measurement of hybridization rate is the $C_0t_{1/2}$ which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0t_{1/2}$ is found graphically by standard procedures familiar to those having an ordinary level of skill in the art.

Preferred Amplification Primers

Primers useful for conducting amplification reactions can have different lengths. For example, amplification oligonucleotides complementary to one strand of the HIV-2 target nucleic acid sequence preferably have lengths of up to 100 bases, more preferably from 18 to 60 bases, still more preferably from 18 to 34, or still more preferably from 18 to 25 bases and include at least 9 and up to 34 contiguous bases substantially complementary to the sequence given by AAAATCCCTAGCAGGTTGGCGCCCGAACAGGGAC (SEQ ID NO:8). Stated in different terms, but identifying the same oligonucleotides, these primers include at least 9 and up to 34 contiguous bases contained in a sequence substantially corresponding to GTCCCTGTTCGGGCGCCAACCTGCTAGGGATTTT (SEQ ID NO:9). Although it is not believed essential for operability of the invention, all of the primers listed in Table 2 share the common core sequence CGGGCGCCA (SEQ ID NO:34). Our finding that mismatches are tolerated between the sequence of SEQ ID NO:9 and the primer sequence located downstream (3') of the sequence of SEQ ID NO:34 shows the general utility of primers having a subset of the sequence of SEQ ID NO:9. In other words, primer sequences which are derived from SEQ ID NO:9 and which hybridize to a target having the sequence of SEQ ID NO:8 under amplification conditions such as those employed herein can be used in the amplification procedures described herein. In general, primers having 9–34 contiguous bases of SEQ ID NO:9 are highly preferred for use as promoter-primers, such as T7 promoter-primers. Of course, if the primer is a T7 promoter-primer there will be included at the 5' end of the primer a T7 promoter sequence which typically adds about 27–33 bases to the length of the primer. Examples of preferred amplification primers in accordance with this aspect of the invention include oligonucleotides having the sequences given by SEQ ID NO:10, SEQ ID NO:11, SEQ ID NO:12, SEQ ID NO:13 and SEQ ID NO:14. One of the oligonucleotide sequences disclosed herein (SEQ ID NO:12) had one nucleotide mismatch and two nucleotide deletions compared with the segment of SEQ ID NO:9 that was present in the primer. Another of the oligonucleotide sequences (SEQ ID NO:13) had a single nucleotide deletion compared with the portion of SEQ ID NO:9 that was present in the oligonucleotide. These sequences also can be found in the T7 promoter-primers having the sequences of SEQ ID NO:17 and 18, respectively. Without taking account of the deletions, these primers respectively had a total of 7 and 5 base mismatches compared with the portions of SEQ ID NO:9 that were present in the oligonucleotides. The T7 promoter-primers disclosed herein are particularly useful for performing nucleic acid amplification reactions using the methods described by Kacian et al., in U.S. Pat. Nos. 5,399,491 and 5,554,516. The disclosures of these patent documents are incorporated herein by reference. Primers optionally may include modified nucleotides or nucleotide analogs. Preferably, detection of amplicons synthesized using these primers is accomplished using the oligonucleotide detection probes disclosed herein.

Other amplification primers, that can be used in any combination with the above-described primers for carrying out amplification reactions, are complementary to the opposite strand of the HIV-2 target nucleic acid sequence. Amplification primers complementary to this opposite strand of the HIV-2 target nucleic acid sequence preferably have lengths of up to 100 bases, or more preferably 19 to 40 bases, or still more preferably 19 to 21 bases. These primers are particularly useful as non-promoter primers. As disclosed herein, these primers have at least 19 contiguous bases from a sequence substantially corresponding to GTGTGTGTTC-CCATCTCTCCTAGTCGCCGCCTGGTCATTC (SEQ ID NO:1). Examples of particular amplification primers fulfilling these conditions include oligonucleotides having the sequences given by SEQ ID NO:2, SEQ ID NO:3, SEQ ID NO:4, SEQ ID NO:5, SEQ ID NO:6 and SEQ ID NO:7.

It should be understood that the above-specified variable lengths of the amplification primers and detection probes are intended to accommodate inclusion of extraneous sequences that may not participate in target binding, and that may not substantially affect amplification or detection procedures. For example, promoter-primers useful for performing amplification reactions in accordance with the invention have at least a minimal sequence that hybridizes to the HIV-2 target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence. Probe sequences should include the 14-mer sequence of SEQ ID NO:21, or the complement thereof, as a common core. This defines a probe-binding domain in the HIV-2 target sequence, or in amplicons synthesized by an amplification procedure. Amplification primers that hybridize downstream of the probe-binding domain should have sequences with at least 9 contiguous bases contained within the sequence of SEQ ID NO:9. Indeed, the results presented herein indicate that the sequence of SEQ ID NO:12 which is complementary to HIV-2 nucleic acids (and which was present in the promoter-primer of SEQ ID NO:17) was sufficient to promote amplification even though this sequence had no more than 9 contiguous bases from SEQ ID NO:9. Finally, amplification primers that hybridize upstream of the probe-binding domain should have at least 19 contiguous bases from the sequence of SEQ ID NO:1.

The following two Tables present specific examples of oligonucleotide sequences that were used as primers for amplifying HIV-2 nucleic acids. Table 1 presents the sequences of non-T7 primers that were complementary to HIV-2 sequences on one strand of nucleic acid. Table 2 presents the sequences of both the HIV-2 target-complementary sequences and the full sequences for T7 promoter-primers that were used during development of the invention. Compared with the oligonucleotide sequences in Table 1, the oligonucleotide sequences in Table 2 are complementary to the opposite nucleic acid strand. As indicated above, all T7 promoter-primers included sequences complementary to an HIV-2 target at their 3' ends, and a T7 promoter sequence at their 5' ends.

TABLE 1

Polynucleotide Sequences of Amplification Primers

| Sequence | Identifier |
| --- | --- |
| GTGTGTGTTCCCATCTCTC | SEQ ID NO:2 |
| TGTGTTCCCATCTCTCCTAG | SEQ ID NO:3 |
| GTTCCCATCTCTCCTAGTCGC | SEQ ID NO:4 |
| TCCTAGTCGCCGCCTGGTCA | SEQ ID NO:5 |
| CCTAGTCGCCGCCTGGTCA | SEQ ID NO:6 |
| TAGTCGCCGCCTGGTCATTC | SEQ ID NO:7 |

Table 2 presents HIV-2 target-complementary oligonucleotide sequences (SEQ ID NOs:10–14) and the respectively corresponding T7 promoter-primer sequences (SEQ ID NOs:15–19).

TABLE 2

Polynucleotide Sequences of Amplification Primers

| Sequence | Identifier |
| --- | --- |
| CGGGCGCCAACCTGCTAGGGATTTT | SEQ ID NO:10 (HIV-2 complementary primer) |
| GTCCCTGTTCGGGCGCCA | SEQ ID NO:11 (HIV-2 complementary primer) |
| CGGGCGCCACTGCTAGAGATTTT | SEQ ID NO:12 (HIV-2 complementary primer) |

TABLE 2-continued

Polynucleotide Sequences of Amplification Primers

| Sequence | Identifier |
| --- | --- |
| CGGGCGCCACCTGCTAGGGATTTT | SEQ ID NO:13 (HIV-2 complementary primer) |
| CCCTGTTCGGGCGCCAACCTGCTAG | SEQ ID NO:14 (HIV-2 complementary primer) |
| AATTTAATACGACTCACTATAGGGAGACGGGCG CCAACCTGCTAGGGATTTT | SEQ ID NO:15 (T7 promoter-primer) |
| AATTTAATACGACTCACTATAGGGAGAGTCCCTG TTCGGGCGCCA | SEQ ID NO:16 (T7 promoter-primer) |
| AATTTAATACGACTCACTATAGGGAGACGGGCG CCACTGCTAGAGATTTT | SEQ ID NO:17 (T7 promoter-primer) |
| GAAATTAATACGACTCACTATAGGGAGACCACA CGGGCGCCACCTGCTAGGGATTTT | SEQ ID NO:18 (T7 promoter-primer) |
| GAAATTAATACGACTCACTATAGGGAGACCACA CCCTGTTCGGGCGCCAACCTGCTAG | SEQ ID NO:19 (T7 promoter-primer) |

Preferred sets of primers for amplifying the HIV-2 LTR region in a transcription-mediated amplification reaction include a first primer that hybridizes the HIV-2 LTR transcript (such as one of the primers listed in Table 2) and a second primer that is complementary to the sequence of an extension product of the first primer (such as one of the primer sequences listed in Table 1). In a highly preferred embodiment, the first primer is a promoter-primer that includes a T7 promoter sequence at its 5' end.

In certain preferred embodiments, a set of at least two amplification primers for amplifying HIV-2 nucleic acid is provided which includes: (i) a first amplification primer comprising an oligonucleotide having or substantially corresponding to the base sequence of SEQ ID NO:10, SEQ ID NO:11, SEQ ID NO:12, SEQ ID NO:13 or SEQ ID NO:14; and (ii) a second amplification primer comprising an oligonucleotide having or substantially corresponding to the base sequence of SEQ ID NO:2, SEQ ID NO:3, SEQ ID NO:4, SEQ ID NO:5, SEQ ID NO:6 or SEQ ID NO:7. In a particularly preferred combination, the first amplification primer is a promoter-primer that comprises an oligonucleotide having or substantially corresponding to the base sequence of SEQ ID NO:10, and the second amplification primer comprises an oligonucleotide having or substantially corresponding to the base sequence of SEQ ID NO:6.

Preferred Detection Probes

One aspect of the invention relates to oligonucleotides that can be used as hybridization probes for detecting HIV-2 nucleic acids. Methods for amplifying a target nucleic acid sequence present in the nucleic acid of HIV-2 can include an additional step for detecting HIV-2 amplicons. This procedure for detecting HIV-2 nucleic acids (including HIV-2 amplicons) includes steps for: contacting a test sample with a hybridization assay probe which preferentially hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of HIV-2 in the test sample. This may involve detecting the probe:target duplex as an indicator of the presence of HIV-2 in the biological sample. Thus, probe compositions and methods employing these compositions fall withing the scope of the present invention.

Hybridization assay probes useful for detecting HIV-2 nucleic acid sequences include a base sequence substantially complementary to an HIV-2 RNA transcript or the encoding DNA.

Thus, probes of the invention hybridize one strand of an HIV-2 target nucleic acid sequence, or the complement thereof. All probes of the present invention stably hybridize an HIV-2 target sequence under stringent hybridization assay conditions. These probes may also have additional bases outside of the targeted nucleic acid region which may or may not be complementary to HIV-2 nucleic acid.

Preferred probes are sufficiently homologous to the target nucleic acid to hybridize under stringent hybridization conditions corresponding to about 60° C. when the salt concentration is in the range of 0.6–0.9 M. Preferred salts include lithium chloride, but other salts such as sodium chloride and sodium citrate also can be used in the hybridization solution. Example high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA.

In certain embodiments of the invention, probes preferably have target-complementary sequences of up to 22 bases, still more preferably up to 18 bases, and still more preferably up to 16 bases; and include between 14 and 22 contiguous nucleotides contained in a sequence substantially corresponding to CCTGGTCTGTTAGGACCCTTCT (SEQ ID NO:20). Notably, each of the probes employed in the Examples disclosed herein contained a common 14 base sequence GTCTGTTAGGACCC (SEQ ID NO:21). Of course, probes of the present invention alternatively can have sequences that are complementary to the foregoing probe sequences. In all cases, when the probes are entirely complementary to HIV-2 nucleic acids (including HIV-2 amplicons), the probe lengths are preferably up to 35 nucleotides, more preferably up to 22 nucleotides, still more preferably up to 18 nucleotides, and even still more preferably up to 16 nucleotides. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Specific Examples of probes that can be used to carry out the assay disclosed herein include oligonucleotides having or substantially corresponding to the base sequences, or complements thereof, given by SEQ ID NO:22, SEQ ID NO:23, SEQ ID NO:24, SEQ ID NO:25, SEQ ID NO:26, and SEQ ID NO:27. It is also preferable for probes in accordance with the present invention to include an acridinium ester label joined to the probe by means of a non-nucleotide linker. For example, a highly preferred probe includes an acridinium ester label joined to the probe through a non-nucleotide linker positioned between nucleotides 9 and 10 (reading 5' to 3') of SEQ ID NO:26.

The following Table presents the sequences of preferred detection probes that were used for detecting HIV-2 amplicons. Since alternative probes for detecting HIV-2 nucleic acid sequences can hybridize the opposite-sense strand of HIV-2, the present invention also includes oligonucleotides that are complementary to the sequences presented in Table 3.

TABLE 3

Polynucleotide Sequences of HIV-2 Amplicon Detection Probes

| Sequence | Sequence Identifier |
| --- | --- |
| CCTGGTCTGTTAGGACCC | SEQ ID NO:22 |
| CTGGTCTGTTAGGACCCT | SEQ ID NO:23 |
| TGGTCTGTTAGGACCCTT | SEQ ID NO:24 |
| GGTCTGTTAGGACCCTTC | SEQ ID NO:25 |
| GTCTGTTAGGACCCTT | SEQ ID NO:26 |
| GTCTGTTAGGACCCTTCT | SEQ ID NO:27 |

In some embodiments of the invention, the probe sequence for detecting amplified LTR sequences includes a methoxy backbone or at least one methoxy linkage in the nucleic acid backbone. Preferably, detection probes are labeled with chemiluminescent AE compounds that are attached to the probe sequences via a linker substantially as described in U.S. Pat. No. 5,585,481; and in U.S. Pat. No. 5,639,604, particularly as described at column 10, line 6 to column 11, line 3, and in Example 8. The disclosures contained in these patent documents are hereby incorporated by reference.

Selection and Use of Capture Oligonucleotides

Preferred capture oligonucleotides include a first sequence that is complementary to an HIV-2 sequence in the LTR region (i.e., an HIV-2-binding sequence) covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucleotide, is used to hybridize to a complementary base sequence to provide a means for capturing the hybridized target HIV-2 nucleic acid in preference to other components in the biological sample.

Although any base sequence that hybridizes to a complementary base sequence may be used in a tail sequence, it is preferred that the hybridizing sequence span a length of about 5 to 50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that specifically binds an HIV-2 target polynucleotide, and a second sequence that specifically binds an oligo(dT) stretch immobilized to a solid support.

Using the components illustrated in FIG. 1, one assay for detecting HIV-2 sequences in a biological sample includes the steps of capturing the target nucleic acid using the capture oligonucleotide, amplifying the captured target region using at least two primers, and detecting the amplified nucleic acid by first hybridizing the labeled probe to a sequence contained in the amplified nucleic acid and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size ± about 5%).

Retrieving the target nucleic acid:capture oligonucleotide:immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Preferred Methods for Amplifying and Detecting HIV-2 Polynucleotide Sequences

Preferred methods of the present invention are described and illustrated by the Examples presented below. With reference to FIG. 1, one system for detecting a target region of the HIV-2 genome (shown by a thick solid horizontal line) is illustrated. This system includes four oligonucleotides (shown by the shorter solid lines): one capture oligonucleotide that includes a sequence that hybridizes specifically to an HIV-2 sequence in the target region and a tail ("T") that hybridizes to complementary sequence immobilized on a solid support to capture the target region present in a biological sample; one T7 promoter-primer which includes a sequence that hybridizes specifically to an HIV-2 sequence in the target region and a T7 promoter sequence ("P") which, when double-stranded, serves as a functional promoter for T7 RNA polymerase;

one non-T7 primer which includes a sequence that hybridizes specifically to a first strand cDNA made from the target region sequence using the T7 primer; and one labeled probe which includes a sequence that hybridizes specifically to a portion of the target region that is amplified using the two primers.

As indicated above, amplifying the captured target region using the two primers can be accomplished using a variety of known nucleic acid amplification reactions. In a preferred embodiment, a transcription-associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription-associated amplification uses two types of primers (one being referred to as a promoter-primer because it contains a promoter sequence, labeled "P" in FIG. 1, for an RNA polymerase) two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription-mediated amplification, the captured target nucleic acid is hybridized to a first primer shown as a T7 promoter-primer. Using reverse transcriptase, cDNA is synthesized from the T7 promoter-primer using the target RNA as a template. The second primer, shown as a non-T7 primer, hybridizes to the cDNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following the cDNA synthesis step to produce additional RNA transcripts, thereby amplifying target region-specific nucleic acid sequences.

The detecting step uses at least one detection probe that binds specifically to the amplified RNA transcripts or amplicons described above. Preferably, the detection probe is labeled with a detectable label that can be detected using a homogeneous detection system. More preferably, the labeled probe is labeled with an acridinium ester compound from which a chemiluminescent signal is produced and detected, as described above.

Kits for Detecting HIV-2 Nucleic Acids

Yet another aspect of the invention relates to kits for performing polynucleotide amplification reactions using HIV-2 nucleic acid templates. Preferably, kits in accordance with the present invention contain a pair of oligonucleotide primers that may be used for amplifying HIV-2 nucleic acids in an in vitro amplification reaction. Exemplary kits may include: (1) a first amplification oligonucleotide that includes a sequence of 9–34 contiguous bases contained within the sequence of SEQ ID NO:9, and that has a length of up to 100 nucleotides; and (2) and a second amplification oligonucleotide that includes a sequence of 19–40 contiguous bases from the sequence of SEQ ID NO:1, and that has a length of up to 100 nucleotides. Of course, shorter amplification oligonucleotides which are disclosed herein also may be packaged into kit formats. The kits may further contain an oligonucleotide detection probe that includes the sequence of SEQ ID NO:21 or the complement thereof. This probe may be of up to 35 nucleotides in length, but alternatively be of up to 22 nucleotides in length or shorter as disclosed herein. Still further, the kits may contain capture oligonucleotides for purifying HIV-2 template nucleic acids away from other species prior to amplification. Exemplary capture oligonucleotides have the sequences of SEQ ID NO:3 1 and SEQ ID NO:32. Indeed, kits useful for practicing the invented method of detecting HIV-2 nucleic acids may include essentially any of the amplification oligonucleotide compositions and/or detection probe compositions disclosed herein in packaged combination with one another.

Multiplex Amplification Reactions

A convenient testing format for detecting multiple analyte polynucleotides involves conducting simultaneous amplification reactions using different primer sets, wherein amplicons synthesized in the reaction are detected by hybridization. In this regard, Gen-Probe Incorporated (San Diego, Calif.) has developed an HIV-1/HCV test that detects HIV-1 and/or HCV (Hepatitis C Virus) nucleic acids in a single-tube multiplex format using three key steps. In an initial sample preparation procedure plasma is treated with detergent to release viral genomic RNA, target-specific oligonucleotides are hybridized to the target and captured onto magnetic microparticles which are separated from plasma in a magnetic field. Next, a transcription-based polynucleotide amplification system is employed to amplify HIV-1 and/or HCV target RNA in a single reaction. Finally, detection is accomplished using nucleic acid hybridization of chemiluminescent probes that are complementary to the HIV-1 or HCV amplicons. If the assay gives a positive result, discriminatory tests are performed to differentiate between the two viruses.

As the number of different primer sets in a multiplex amplification reaction increases, with each set of primers being specific for a different analyte polynucleotide, there is an increased opportunity for undesired interaction among primers and between primers and irrelevant amplicons. The primer sequences disclosed herein advantageously can be used as reagents in a single polynucleotide amplification reaction which is also capable of amplifying virus-specific sequences from HIV-1, hepatitis B virus (HBV) and hepatitis C virus (HCV).

The general principles of the present invention may be more fully appreciated by reference to the following non-limiting Examples. The first Example describes procedures for identifying useful amplification primers.

Preferred primer combinations for amplifying polynucleotide sequences of the HIV-2 long terminal repeat (LTR) were identified in a series of procedures that employed different numbers of nucleic acid template molecules. As described below, an initial test was performed using a synthetic HIV-2 template at a level of 5,000 copies/reaction. Subsequent tests carried out using either 100 or 500 copies/ reaction provided information about sensitivity of the assay. Analysis of results from replicate trials yielded average values for amplicon production as well as information about reproducibility of the procedure. T7 promoter-primers and non-T7 primers were screened in combination using the solution-phase procedure described below. Although the below-described procedures were particularly carried out using a Transcription Mediated Amplification (TMA) protocol, the primers disclosed herein may be used to produce amplicons by alternative methods that will be familiar to those having an ordinary level of skill in the art.

Example 1 describes the methods used for identifying primers that amplified HIV-2 polynucleotide sequences.

EXAMPLE 1

Identification of Amplification Primers

In vitro transcribed RNA that included the sequence of bases 1–644 of the HIV-2 HIV2FG subtype LTR (GenBank accession number J03654) was prepared using a linearized plasmid clone as a template according to standard laboratory procedures. The resulting in vitro transcripts were then used as a template in amplification reactions that employed paired sets of primers in TMA reactions essentially as described by Kacian et al., in U.S. Pat. No. 5,399,491. Each promoter-primer included either a T7 promoter sequence AATT-TAATACGACTCACTATAGGGAGA (SEQ ID NO:28) or GAAATTAATACGACTCACTATAGGGAGACCACA (SEQ ID NO:29) at the 5' end, and a target-complementary sequence at the 3' end. Amplification reactions were initially conducted for some of the primer combinations using 5,000 copies of the synthetic RNA template and 15 pmols of each primer in 100 μl of standard reaction buffer. The target nucleic acid and primers were heated to 60° C. for 10 minutes and then cooled to 42° C. to facilitate primer annealing. Moloney Murine Leukemia Virus (MMLV) reverse transcriptase (2000 units) and T7 RNA polymerase (2000 units) were then added to the mixtures. The final amplification reactions contained 50 mM Tris HCl (pH 8.5), 35 mM KCl, 4 mM GTP, 4 mM ATP, 4 mM UTP, 4 mM CTP, 1 mM dATP, 1 mM dTTP, 1 mM dCTP, 1 mM dGTP, 20 mM $MgCl_2$, 20 mM N-Acetyl-L-Cysteine, and 5% (w/v) glycerol. After a one hour incubation at 42° C., the entire 100 μl amplification reaction was assayed by hybridization essentially as described by Arnold et al., in U.S. Pat. No. 5,639,604, the disclosure of which is incorporated herein by reference, using an acridinium ester labeled probe in a homogeneous protection assay. A probe having the sequence of SEQ ID NO:27 was labeled with AE to a specific activity of $1.94 \times 10^8$ RLU/pmol and then used in an amount equivalent to $1.9 \times 10^7$ RLU for each hybridization reaction to detect HIV-2 amplicons. Probe hybridization was performed in 200 μl of a solution containing 0.05M lithium succinate (pH 5), 0.6M LiCl, 1% (w/v) lithium lauryl sulfate, 10 mM EDTA, 10 mM EGTA, at 60° C. for 15 minutes, followed by addition of 300 μl of 0.15 M sodium tetraborate (pH 8.5), 1% TRITON® X-100 (Union Carbide Corporation; Danbury, Conn.). This mixture was first incubated at 60° C. for 10 minutes to inactivate unhybridized probe, and thereafter cooled to room temperature. The remaining chemiluminescence in each sample was assayed using a Gen-Probe LEADER® I luminometer configured for automatic injection of 1 mM nitric acid and 0. 1% (v/v) hydrogen peroxide followed by injection of a solution containing 1 N sodium hydroxide. Results measured for the chemiluminescent reaction were expressed in Relative Light Units (RLU).

Table 4 presents results from amplification procedures that were conducted using 5,000 copies of template polynucleotide. Notably, the promoter-primer having the sequence of SEQ ID NO:17 efficiently amplified HIV-1 polynucleotide sequences (data not shown) and was included in the present procedure to determine whether HIV-1 and HIV-2 nucleic acids could be co-amplified using a common primer. The sequence of this primer spans a region of sequence where HIV-1 and HIV-2 differ by an insertion/deletion. Thus, compared with the sequence of SEQ ID NO:9 (from which promoter-primer sequences of the present invention are derived), the HIV-2 target-complementary portion of the promoter-primer has a mismatch at nucleotide position 28 and a two nucleotide deletion corresponding to the AC nucleotide pair at positions 19–20 in the sequence of SEQ ID NO:9. Results shown in the table are derived from replicates of 4 trials (for the promoter-primer having the sequence of SEQ ID NO:16) or 5 trials (for the promoter-primers having the sequences of SEQ ID NOs:15 and 17) of the amplification and detection procedure. Some of the negative control ("Neg. control") entries shown in the table were obtained from assays that were carried out at different times. All negative control values were obtained from trials conducted in the absence of any HIV-2 template. In view of the highly reproducible nature of the assay, we reasonably assumed that the magnitude of the negative control reactions also would be comparable across different experiments. Data that is not available is represented in the table by "NA".

TABLE 4

Amplification of HIV-2 Polynucleotide Sequences Using Different Primer Combinations

| T7 Promoter- | | Non T7 Primer Identifier | | |
|---|---|---|---|---|
| Primer Identifier | Result | SEQ ID NO:2 | SEQ ID NO:3 | SEQ ID NO:7 |
| SEQ ID NO:15 | Avg. RLU | 12,002,375 | 11,450,076 | 11,701,970 |
| | Neg. control | 400,916 | 27,993 | 53,954 |
| | % CV | 4 | 7 | 5 |
| SEQ ID NO:16 | Avg. RLU | 12,160,598 | 4,894,812 | 11,501,174 |
| | Neg. control | NA | NA | 29,936 |
| | % CV | 5 | 5 | 6 |
| SEQ ID NO:17 | Avg. RLU | 9,712,454 | 4,989,813 | 11,032,883 |
| | Neg. control | NA | 115,172 | NA |
| | % CV | 15 | 62 | 6 |

The results presented in Table 4 showed that each of the primer combinations tested at template levels of 5,000 copies/reaction gave positive results. Although all of the promoter-primers in the procedure gave easily detectable amplification signals, the promoter-primer identified as SEQ ID NO:15 advantageously gave good results when used in combination with each of the non-T7 primers that was tested. Notably, amplification reactions that included the promoter-primer having the sequence of SEQ ID NO:15 uniformly were associated with low % CV values, thereby indicating a high degree of reproducibility and particular robustness of amplification reactions that included this primer. Interestingly, the results shown in the table indicated that even the promoter-primer having the sequence of SEQ ID NO:17, which amplifies HIV-1 sequences in a highly efficient manner, also amplified HIV-2 sequences in this procedure.

Based on the findings presented in Table 4, further testing was carried out using additional promoter-primers and lower levels of input template to demonstrate flexibility with respect to the design of useful promoter-primers and sensitivity of the assay. More particularly, the above-described amplification and detection procedures were repeated using the promoter-primers having the sequences of SEQ ID NOs:15 and 17 in combination with non-T7 primers and either 100 or 500 copies of the HIV-2 template in each reaction. Thereafter, one of the non-T7 primers was selected for testing in combination with a collection of T7 promoter-primers that possessed T7 promoter sequences and target-complementary sequences different from those present in any of the promoter-primers having sequences identified by SEQ ID NOs:15–17. Results from these procedures are presented in Tables 5–8.

The results presented in Tables 5 and 6 confirmed that the promoter-primer identified by SEQ ID NO:15 efficiently amplified HIV-2 polynucleotide sequences with each of the indicated non-T7 primers, even at input template levels of only 100 copies/reaction. The promoter-primer having the sequence of SEQ ID NO:17 also was useful as a component in the amplification reaction, although at a level somewhat reduced level compared to the promoter-primer having the sequence of SEQ ID NO:15. Clearly though, these two primers defined a region of the LTR that was useful as a target for primer-binding in the HIV-2 nucleic acid amplification assay.

Three additional non-T7 primers were synthesized and tested in combination with the promoter-primer of SEQ ID NO:15 in the HIV-2 amplification assay. These additional primers had the sequences given by SEQ ID NOs:4–6, where positions 1–4 of each oligonucleotide were occupied by 2' methoxy residues. Table 7 presents results obtained when these primer sets were tested in the above-described amplification protocol using 100 copies of the synthetic HIV-2 template RNA in each reaction and the amplification products detected essentially as described above.

TABLE 5

Amplification of HIV-2 Polynucleotide Sequences at 500 Copies/Reaction Using Different Primer Combinations

| T7 Promoter-Primer Identifier | Result | Non T7 Primer Identifier | | |
|---|---|---|---|---|
| | | SEQ ID NO:2 | SEQ ID NO:3 | SEQ ID NO:7 |
| SEQ ID NO:15 | Avg. RLU | 11,551,224 | 11,709,201 | 10,728,899 |
| | Neg. control | 91,900 | 84,559 | 93,300 |
| | % CV | 7 | 3 | 10 |
| SEQ ID NO:17 | Avg. RLU | 158,707 | 2813,144 | 1,416,150 |
| | Neg. control | NA | 115,172 | 99,001 |
| | % CV | 19 | 128 | 182 |

TABLE 6

Amplification of HIV-2 Polynucleotide Sequences at 100 Copies/Reaction Using Different Primer Combinations

| T7 Promoter-Primer Identifier | Result | Non T7 Primer Identifier | | |
|---|---|---|---|---|
| | | SEQ ID NO:2 | SEQ ID NO:3 | SEQ ID NO:7 |
| SEQ IN NO:15 | Avg. RLU | 10,805,600 | 9,581,007 | 11,022,067 |
| | Neg. control | 91,900 | 84,559 | 93,300 |
| | % CV | 11 | 17 | 4 |
| SEQ IN NO:17 | Avg. RLU | 1,710,494 | 129,235 | 846,399 |
| | Neg. control | 497,960 | 115,172 | 99,001 |
| | % CV | 184 | 19 | 165 |

TABLE 7

Amplification of HIV-2 Polynucleotide Sequences at 100 Copies/Reaction Using Different Primer Combinations

| T7 Promoter-Primer Identifier | Result | Non-T7 Primer Identifier | | |
|---|---|---|---|---|
| | | SEQ ID NO:4 | SEQ ID NO:5 | SEQ ID NO:6 |
| SEQ ID NO:15 | Avg. RLU | 15,143,148 | 15,149,932 | 13,731,644 |
| | Neg. control | 133,313 | 82,829 | 11,547 |
| | % CV | 4.3 | 5.5 | 8.5 |

The results presented in Table 7 showed that all three primer combinations gave exceptionally good results in the amplification procedure. Notably, the combination of the primer having the sequence of SEQ ID NO:6 and the promoter-primer having the sequence of SEQ ID NO:15 efficiently amplified the HIV-2 template sequence and advantageously gave a very low reading for the negative control reaction. Each of the primers and primer combinations disclosed herein represents a preferred embodiment of the invention. The combination of the primer having the sequence of SEQ ID NO:6 and the promoter-primer having the sequence of SEQ ID NO:15 is a highly preferred combination for amplifying HIV-2 polynucleotide sequences.

Finally, the primer having the sequence of SEQ ID NO:6 was tested in combination with promoter-primers identified by SEQ ID NOs:18 and 19 in amplification reactions that were conducted using either 500 or 100 copies/reaction of the HIV-2 template. Significantly, both the target-complementary sequence and the T7 promoter sequence in the two primers differed from the T7 promoter sequence employed in the promoter-primers of SEQ ID NOs:15–17. Also significant is the fact that the promoter-primer identified by SEQ ID NO:18 contains a single base deletion corresponding to the A residue at position 19 of the sequence given by SEQ ID NO:9. The numerical values presented in Table 8 are respectively the results of 5 and 4 replicate trials conducted using 500 and 100 copies/reaction or HIV-2 target.

500 copies/reaction of the HIV-2 target. Remarkably, the probe hybridization signals measured in the negative control reactions that included these promoter-primers advantageously were very low. The results further demonstrated that different T7 promoter sequences could be used in the amplification procedure with good results.

The aggregated results presented in Tables 3–7 showed that the LTR target region bound by each of the above-described non-T7 primers defined a domain that could be used for designing additional primers for use in combination with T7 promoter-primers to amplify HIV-2 sequences. This domain encompassed the 40 nucleotide long sequence given by GTGTGTGTTCCCATCTCTCCTAGTCGC-CGCCTGGTCATTC (SEQ ID NO:1). Oligonucleotide having sequences substantially corresponding to this sequence, or a subset thereof, can be used as primers in the amplification reactions described herein. Additionally, the results in Tables 4–8 showed that the LTR target region bound by each of the above-described T7 promoter-primers defined a domain that could be used in combination with non-T7 primers to amplify HIV-2 sequences. This domain encompassed the 34 nucleotide long sequence AAAATCCCTAG-CAGGTTGGCGCCCGAACAGGGAC (SEQ ID NO:8). Oligonucleotides complementary to this sequence, or to a sequence substantially complementary to this sequence, can be used as primers in the amplification reactions described herein.

TABLE 8

Amplification of HIV-2 Polynucleotide Sequences at 500 or 100 Copies/Reaction Using Different Primer Combinations

| T7 Promoter-Primer Identifier | HIV-2 Target Copy Number | Result | Non T7 Primer Identifier SEQ ID NO:6 |
|---|---|---|---|
| SEQ ID NO:18 | 500 | Avg. RLU | 2,800,000 |
| | | Neg. control | 4,778 |
| | | % CV | 8 |
| | 100 | Avg. RLU | 2,800,000 |
| | | Neg. control | 7,367 |
| | | % CV | 6 |
| SEQ ID NO:19 | 500 | Avg. RLU | 2,700,000 |
| | | Neg. control | 2,710 |
| | | % CV | 10 |
| | 100 | Avg. RLU | 2,800,000 |
| | | Neg. control | 36,207 |
| | | % CV | 8 |

The results presented in Table 8 demonstrated that both of the T7 promoter-primers identified by SEQ ID NOs:18–19 gave good results in the amplification assay, with positive signals ranging from 500–1,000 fold above the signals measured in the negative control reactions conducted using Example 2 describes the methods used to identify probes that were useful for detecting HIV-2 amplicons. In this procedure a single synthetic oligonucleotide target complementary to a series of different probe sequences served as a target in a probe-binding assay.

EXAMPLE 2

Oligonucleotide Probes for Detecting HIV-2

A synthetic antisense HIV-2 oligonucleotide having the sequence GAAGGGUCCUAACAGACCAGGGUCUUG-UUA (SEQ ID NO:30) was prepared using 2' methoxy nucleotides according to standard laboratory procedures. This oligonucleotide served as a model RNA target. Six different oligonucleotides that were prepared using 2' methoxy nucleotides and tested as probes had the sequences given in Table 3.

Hybridization reactions consisted of 100 μl volumes of probe protection buffer containing amounts of AE-labeled probe corresponding to 1×10$^6$ RLUs and 100 μl containing 2 pmols of the synthetic HIV-2 RNA target. The buffer solution included 75 mM succinic acid, 129 mM lithium lauryl sulfate, 75 mM lithium hydroxide, 15 mM aldrithiol-2, 1.0 M lithium chloride, 1 mM EDTA 3% v/v ethyl alcohol, and was pH-adjusted to 4.2. Mixtures were hybridized for 15 minutes at 60° C. and then selected with 250 μl of selection reagent solution that included 600 mM boric acid, 235 mM NaOH and 1% vol/vol TRITON X-100 (the solution having been adjusted to pH 9) for 10 minutes, and then cooled to room temperature for 10 minutes. Negative control hybridization reactions omitted the antisense HIV-2 target oligonucleotide. Chemiluminescence that reflected the amount of AE label associated with hybridized probe was determined using the method described above. The results from this procedure are presented in Table 9.

probes, such as molecular beacons, having particular secondary structures. Since the sequence of SEQ ID NO:20 is derived from a portion of the HIV-2 genome that is absent from the genome of HIV-1, these probes are specific for HIV-2 and not HIV-1.

Notably, probes having the sequences of SEQ ID NOs:26 and 25 gave unusually good results in this procedure. The oligonucleotide sequences of these probes are highly preferred for use in the detection step of the assay described above. Of course, the positioning of any detectable label can be varied and still fall within the scope of the invention. For example, it is highly preferred to use a probe having the sequence of SEQ ID NO:26 with an AE label linked between positions 9 and 10 for detection of HIV-2 amplicon using the procedures described above.

Methods for determining whether candidate oligonucleotides could be used to capture HIV-2 nucleic acids from solution were carried out using the above-described in vitro transcribed HIV-2 RNA as a model target. Each of two different candidate capture oligonucleotides included an HIV-2 specific sequence linked to an oligo-(dA) stretch. When combined with the HIV-2 RNA target and magnetic particles modified to display oligo-(dT), a functional capture oligonucleotide bridged the HIV-2 target and the particle and immobilized the HIV-2 target. Removing the particulate complexes from solution effectively represented a means for enriching the HIV-2 template. In the procedure described in the following Example, two capture oligonucleotides were separately contacted with the HIV-2 RNA and magnetic particles modified with oligo-(dT). After collecting and then

TABLE 9

Probe Hybridization Results

| Hybridization | Average Hybridization (% of Input) | | | | |
|---|---|---|---|---|---|
| Reaction | SEQ ID NO:22 | SEQ ID NO:23 | SEQ ID NO:24 | SEQ ID NO:25 | SEQ ID NO:26 |
| Negative Control | 0.07 | 0.22 | 0.10 | 0.09 | 0.06 |
| Synthetic HIV-2 RNA Amplicon | 22 | 15 | 21 | 54 | 97 |

As indicated by the results presented in Table 9, each of the probes tested in the procedure gave low levels of background hybridization and at least moderate levels of positive reaction with the HIV-2 target sequence. More particularly, the negative control values were all lower than 0.25%, while the reactions conducted in the presence of the HIV-2 target sequence were all greater than 15% of the input level of probe. Taken together with the showing in Example 1 that the a probe having the sequence of SEQ ID NO:27 was useful for detecting HIV-2 amplicons, the results in Table 9 showed that all of the sequences presented in Table 3 were useful as detection probes.

The success achieved in the above procedure defined an HIV-2 sequence domain that could be used for designing additional detection probes. More particularly, this domain extended over the 22 nucleotide long stretch having the sequence CCTGGTCTGTTAGGACCCTTCT (SEQ ID NO:20). Oligonucleotides having sequences substantially corresponding to this sequence, a subset thereof, or the complement thereof, can be used as probes for detecting HIV-2 nucleic acids. Of course, useful probes may be longer than the length of this domain, and the HIV-2 complementary portion of useful probes may be incorporated into washing the particles, bound HIV-2 sequences were detected in homogenous protection assays. In each instance, the capture oligonucleotide immobilized the HIV-2 RNA target onto the magnetic particle.

The following Example describes methods that were used for identifying HIV-2 capture oligonucleotides.

EXAMPLE 3

Detection of HIV-2 Target Sequences Using Capture Oligonucleotides $5 \times 10^{11}$ copies of an in vitro transcribed HIV-2 LTR RNA target (described above) were dispersed in 400 μl of lysis/capture buffer containing either 0, 1.5 pmols, 3.5 pmols or 5 pmols of capture oligonucleotides having the sequences of SEQ ID NOs:31 and 32, and about 100 μg of immobilized poly-(dT$_{14}$) linked to paramagnetic particles (0.7–1.05 μ particles, Seradyn, Indianapolis, Ind.). The lysis/capture buffer included 790 mM HEPES, 230 mM succinic acid, 10% (w/v) lithium lauryl sulfate, 680 mM lithium hydroxide monohydrate. The capture oligonucleotide having the sequence of SEQ ID NO:31 had positions 1–20 occupied by 2'-methoxy nucleotide analogs and positions 21–53 occupied by deoxyribonucleotides. The capture oligonucleotide having the sequence of SEQ ID NO:32 had positions 1–18 occupied by 2'-methoxy nucleotide analogs and positions 19–51 occupied by deoxyribonucleotides. A spacer represented by the sequence 5'-TTT-3' was interposed between the HIV-2 complementary sequence and the poly(A) tail region for each of the capture oligonucleotides. The poly-(dT$_{14}$) was linked to the paramagnetic particles using carbodiimide chemistry as described by Lund et al., in *Nuc. Acids Res.* 16:10861–10880 (1988). The mixtures were heated at 55–60° C. for about 15 to 30 minutes and then cooled to room temperature to allow hybridization. A magnetic field was applied to collect the particle complexes containing immobilized capture oligonucleotide and HIV-2 RNA using procedures such as those described by Wang in U.S. Pat. No. 4,895,650. The particles were washed twice with 1 ml of a washing buffer (10 mM HEPES, 6.5 mM NaOH, 1 mM EDTA, 0.3% (v/v) ethanol, 0.02% (w/v) methyl-paraben, 0.01% (w/v) propyl-paraben, 150 mM NaCl, 0.1% (w/v) sodium lauryl sulfate) by resuspension and repetition of the magnetic separation step. Washed particles were suspended in 100 µl of hybridization buffer, and the mixture subjected to the probe hybridization and detection procedure described in the previous Example, except that a probe having the sequence SEQ ID NO:33 was used instead of a probe having the sequence of SEQ ID NO:27. For each assay condition, a mock capture control indicated the maximum chemiluminescence value that could be achieved in the assay. Table 10 presents the chemiluminescence measurements for replicates of two assays for each level of capture oligonucleotide.

the mixture also contains about 3.5 pmols of capture oligonucleotide having the sequence of SEQ ID NO:31 and about 100 µg of immobilized poly-dT$_{14}$ probe attached to paramagnetic particles (0.7–1.05 µ particles, Seradyn, Indianapolis, Ind.). The mixture is heated at 55–60° C. for about 15 to 30 minutes and then cooled to room temperature to allow hybridization. A magnetic field is then applied to collect particle complexs. Particles are washed twice with 1 ml of a washing buffer and then resuspended in 75 µl of a nucleic acid amplification reagent solution for transcription associated amplification using methods substantially as described by Kacian et al., in U.S. Pat. Nos. 5,399,491 and 5,554,516.

Briefly, the washed particles with the attached complexes are mixed with 15 pmol each of amplification oligonucleotides having the sequences of SEQ ID NOs:15 and 6 in a reaction mixture (40 mM Tris base (pH 7.5), 17.5 mM KCl, 20 mM MgCl$_2$, 5% polyvinylpyrrolidone (PVP), 1 mM each dNTP, 4 mM each rNTP), covered with a layer of inert oil to prevent evaporation, incubated at 60° C. for 10 minutes, and then at 41.5–42° C. for 10 minutes. Enzymes (about 3,000 Units of MMLV reverse transcriptase and about 3,000 of Units T7 RNA polymerase per reaction) are added, mixed, and the target HIV-2 nucleic acid amplified at 41.5–42° C. for 1 hour.

Amplified HIV-2 target sequences are hybridized with an AE-labeled probe having the sequence of SEQ ID NO:26 and then detected by chemiluminescence and the results expressed in relative light units (RLU) substantially as described previously. For each assay condition, negative controls have an equal volume of plasma that contained no

TABLE 10

Efficiency of Target Capture

| Capture Oligonucleotide | Result | Amount of Capture Oligonucleotide/Reaction | | |
|---|---|---|---|---|
| | | 1.5 pmols | 3.5 pmols | 5 pmols |
| SEQ ID NO:31 | Avg. RLU | 214,064 | 210,545 | 1,033,935 |
| | % Efficiency | 18.4 | 18.1 | 88.9 |
| | % CV | 5 | 6 | 13 |
| SEQ ID NO:32 | Avg. RLU | 126,948 | 174,640 | 1,334,771 |
| | % Efficiency | 10.9 | 15.0 | 114.81 |
| | % CV | 16 | 13 | 4 |

The results presented in Table 10 confirmed that both of the oligonucleotides tested in the procedure could be used for capturing the HIV-2 RNA from solution.

Example 4 describes procedures that can be followed to detect HIV-2 nucleic acids in a biological sample. Although this Example describes a control sample containing a known amount of HIV-2 nucleic acids, it is to be understood that a sample of plasma obtained from a human donor blood sample could be substituted. A positive hybridization result in the latter case would indicate the presence of HIV-2 nucleic acids in the donor sample.

EXAMPLE 4

Detection of HIV-2 Nucleic Acids Using Nucleic Acid Amplification

A first sample of human plasma containing a known amount of HIV-2 (100 copies of HIV-2 per reaction tube) is mixed with an equal volume of a lysis/capture buffer, as described in Example 3. To capture the HIV-2 target RNA, HIV-2 nucleic acid substituted for the HIV-2 containing samples. The detected RLU readings of these assays are then compared.

Results from these procedures show that HIV-2 nucleic acid sequences can be readily detected in a biological sample using the methods of the present invention. More particularly, negative control samples give probe hybridization results corresponding to background signals only. Conversely, samples containing HIV-2 nucleic acids give hybridization signals that are several fold greater than the background. This indicates that the amplification and detection reactions are operable.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A kit for detecting HIV-2 nucleic acids, comprising a packaged combination of the following components in one or more containers:
   (a) a first amplification oligonucleotide that consists of SEQ ID NO:10 and optionally comprises a 5' promoter sequence non-complementary to the HIV-2 nucleic acid; and
   (b) a second amplification oligonucleotide comprising a sequence of 19–40 contiguous bases from the sequence of SEQ ID NO:1, said second amplification oligonucleotide having a length of up to 100 nucleotides.

2. The kit of claim 1, further comprising:
   (c) an oligonucleotide detection probe that comprises the sequence of SEQ ID NO:21 or the complement thereof, and a detectable label.

3. The kit of claim 1, wherein the length of the second amplification oligonucleotide is 19–40 nucleotides.

4. The kit of claim 3, wherein the length of the first amplification oligonucleotide is up to 60 nucleotides.

5. The kit of claim 3, wherein the length of the first amplification oligonucleotide is up to 60 nucleotides, wherein the first amplification oligonucleotide includes said optional 5' promoter sequence.

6. The kit of claim 3, wherein the length of the second amplification oligonucleotide is 19–21 nucleotides.

7. The kit of claim 4, wherein the length of the second amplification oligonucleotide is 19–21 nucleotides.

8. The kit of claim 5, wherein the first amplification oligonucleotide is the promoter-primer of SEQ ID NO:15.

9. The kit of claim 7, wherein the second amplification oligonucleotide is selected from the group consisting of SEQ ID NO:2, SEQ ID NO:3, SEQ ID NO:4, SEQ ID NO:5, SEQ ID NO:6 and SEQ ID NO:7.

10. The kit of claim 7, wherein the first amplification oligonucleotide includes said optional 5' promoter sequence.

11. The kit of claim 10, wherein the first amplification oligonucleotide is the promoter-primer of SEQ ID NO:15.

12. The kit of claim 10, wherein the second amplification oligonucleotide is selected from the group consisting of SEQ ID NO:2, SEQ ID NO:3, SEQ ID NO:4, SEQ ID NO:5, SEQ ID NO:6 and SEQ ID NO:7.

13. The kit of claim 11, wherein the second amplification oligonucleotide is selected from the group consisting of SEQ ID NO:2, SEQ ID NO:3, SEQ ID NO:4, SEQ ID NO:5, SEQ ID NO:6 and SEQ ID NO:7.

14. The kit of claim 11, wherein the length of the first amplification oligonucleotide is 25 nucleotides, and wherein the length of the second amplification oligonucleotide is 19–21 nucleotides.

15. The kit of claim 14, wherein the second amplification oligonucleotide is selected from the group consisting of SEQ ID NO:2, SEQ ID NO:3, SEQ ID NO:4, SEQ ID NO:5, SEQ ID NO:6 and SEQ ID NO:7.

16. The kit of claim 14, wherein the second amplification oligonucleotide is selected from the group consisting of SEQ ID NO:2, SEQ ID NO:3, SEQ ID NO:4, SEQ ID NO:5, SEQ ID NO:6 and SEQ ID NO:7.

17. The kit of claim 2, wherein said oligonucleotide detection probe has a length of up to 18 nucleotides.

18. The kit of claim 17, wherein the sequence of said oligonucleotide detection probe is selected from the group consisting of SEQ ID NO:22, SEQ ID NO:23, SEQ ID NO:24, SEQ ID NO:25, SEQ ID NO:26 and SEQ ID NO:27.

19. The kit of claim 18, wherein the sequence of the first amplification oligonucleotide is SEQ ID NO:10 or SEQ ID NO:15, wherein the sequence of the second amplification oligonucleotide is selected from the group consisting of SEQ ID NO:2, SEQ ID NO:3, SEQ ID NO:4, SEQ ID NO:5, SEQ ID NO:6 and SEQ ID NO:7, and wherein the sequence of the oligonucleotide detection probe is selected from the group consisting of SEQ ID NO:22, SEQ ID NO:23, SEQ ID NO:24, SEQ ID NO:25, SEQ ID NO:26 and SEQ ID NO:27.

20. The kit of claim 2, wherein said oligonucleotide detection probe has a length of up to 35 nucleotides.

21. The kit of claim 20, wherein the length of said oligonucleotide detection probe is up to 22 nucleotides.

22. The kit of claim 21, wherein said oligonucleotide detection probe comprises at least 16 contiguous nucleotides contained within the sequence of SEQ ID NO:20 or the complement thereof.

23. The kit of claim 22, wherein said oligonucleotide detection probe has the sequence of SEQ ID NO:20 or the complement thereof.

24. The kit of claim 22, wherein said oligonucleotide detection probe has a length of up to 18 nucleotides.

25. The kit of claim 24, wherein the length of said oligonucleotide detection probe is 18 nucleotides.

26. The kit of claim 24, wherein said oligonucleotide detection probe has a sequence selected from the group consisting of SEQ ID NO:22 or the complement thereof, SEQ ID NO:23 or the complement thereof, SEQ ID NO:24 or the complement thereof, SEQ ID NO:25 or the complement thereof, SEQ ID NO:26 or the complement thereof, and SEQ ID NO:27 or the complement thereof.

27. The kit of claim 20, wherein said oligonucleotide detection probe comprises DNA.

28. The kit of claim 20, wherein said oligonucleotide detection probe comprises at least one nucleotide analog.

29. The kit of claim 28, wherein said at least one nucleotide analog comprises a methoxy group at the 2' position of a ribose moiety.

30. The kit of claim 26, wherein the detectable label is a chemiluminescent label or a radiolabel.

31. The kit of claim 30, wherein the detectable label is an acridinium ester.

* * * * *

SEQUENCE LISTING

<160> NUMBER OF SEQ ID NOS: 34

<210> SEQ ID NO 1
<211> LENGTH: 40
<212> TYPE: DNA
<213> ORGANISM: HIV-2

<400> SEQUENCE: 1
gtgtgtgttc ccatctctcc tagtcgccgc ctggtcattc                    40

<210> SEQ ID NO 2
<211> LENGTH: 19
<212> TYPE: DNA
<213> ORGANISM: HIV-2

<400> SEQUENCE: 2
gtgtgtgttc ccatctctc                                          19

<210> SEQ ID NO 3
<211> LENGTH: 20
<212> TYPE: DNA
<213> ORGANISM: HIV-2

<400> SEQUENCE: 3
tgtgttccca tctctcctag                                         20

<210> SEQ ID NO 4
<211> LENGTH: 21
<212> TYPE: DNA
<213> ORGANISM: HIV-2

<400> SEQUENCE: 4
gttcccatct ctcctagtcg c                                       21

<210> SEQ ID NO 5
<211> LENGTH: 20
<212> TYPE: DNA
<213> ORGANISM: HIV-2

<400> SEQUENCE: 5
tcctagtcgc cgcctggtca                                         20

<210> SEQ ID NO 6
<211> LENGTH: 19
<212> TYPE: DNA
<213> ORGANISM: HIV-2

<400> SEQUENCE: 6
cctagtcgcc gcctggtca                                          19

<210> SEQ ID NO 7
<211> LENGTH: 20
<212> TYPE: DNA
<213> ORGANISM: HIV-2

<400> SEQUENCE: 7
tagtcgccgc ctggtcattc                                         20

<210> SEQ ID NO 8
<211> LENGTH: 34
<212> TYPE: DNA
<213> ORGANISM: HIV-2

```
<400> SEQUENCE: 8 aaaatccta gcaggttggc gcccgaacag ggac                          34

<210> SEQ ID NO 9
<211> LENGTH: 34
<212> TYPE: DNA
<213> ORGANISM: HIV-2

<400> SEQUENCE: 9
gtccctgttc gggcgccaac ctgctaggga tttt                         34

<210> SEQ ID NO 10
<211> LENGTH: 25
<212> TYPE: DNA
<213> ORGANISM: HIV-2

<400> SEQUENCE: 10
cgggcgccaa cctgctaggg atttt                                   25

<210> SEQ ID NO 11
<211> LENGTH: 18
<212> TYPE: DNA
<213> ORGANISM: HIV-2

<400> SEQUENCE: 11
gtccctgttc gggcgcca                                           18

<210> SEQ ID NO 12
<211> LENGTH: 23
<212> TYPE: DNA
<213> ORGANISM: Artificial Sequence
<220> FEATURE:
<223> OTHER INFORMATION: Primer mismatches HIV-2 sequence by deletion of
      two nucleotides and mutation at a third position

<400> SEQUENCE: 12 cgggcgccac

-continued primer sequence

<400> SEQUENCE: 15
aatttaatac gactcactat agggagacgg gcgccaacct gctagggatt tt        52

<210> SEQ ID NO 16
<211> LENGTH: 45
<212> TYPE: DNA
<213> ORGANISM: Artificial Sequence
<220> FEATURE:
<223> OTHER INFORMATION: T7 promoter primer having a promoter sequence
      appended at the 5' end of an HIV-2 complementary
      primer sequence

<400> SEQUENCE: 16
aatttaatac gactcactat agggagagtc cctgttcggg cgcca               45

<210> SEQ ID NO 17
<211> LENGTH: 50
<212> TYPE: DNA
<213> ORGANISM: Artificial Sequence
<220> FEATURE:
<223> OTHER INFORMATION: T7 promoter primer having a promoter sequence
      appended at the 5' end of the sequence given as
      SEQ ID NO:12

<400> SEQUENCE: 17
aatttaatac gactcactat agggagacgg gcgccactgc tagagatttt           50

<210> SEQ ID NO 18
<211> LENGTH: 57
<212> TYPE: DNA
<213> ORGANISM: Artificial Sequence
<220> FEATURE:
<223> OTHER INFORMATION: T7 promoter primer having a promoter sequence
      appended at the 5' end of the sequence given as
      SEQ ID NO:13

<400> SEQUENCE: 18
gaaattaata cgactcacta tagggagacc acacgggcgc cacctgctag ggatttt    57

<210> SEQ ID NO 19
<211> LENGTH: 58
<212> TYPE: DNA
<213> ORGANISM: Artificial Sequence
<220> FEATURE:
<223> OTHER INFORMATION: T7 promoter primer having a promoter sequence
      appended at the 5' end of an HIV-2 complementary
      primer sequence

<400> SEQUENCE: 19
gaaattaata cgactcacta tagggagacc acacctgtt cgggcgccaa cctgctag    58

<210> SEQ ID NO 20
<211> LENGTH: 22
<212> TYPE: DNA
<213> ORGANISM: HIV-2

<400> SEQUENCE: 20
cctggtctgt taggaccctt ct                                         22

<210> SEQ ID NO 21
<211> LENGTH: 14
<212> TYPE: DNA
<213> ORGANISM: HIV-2

<400> SEQUENCE: 21

```
gtctgttagg accc                                                       14

<210> SEQ ID NO 22
<211> LENGTH: 18
<212> TYPE: DNA
<213> ORGANISM: HIV-2

<400> SEQUENCE: 22
cctggtctgt taggaccc                                                   18

<210> SEQ ID NO 23
<211> LENGTH: 18
<212> TYPE: DNA
<213> ORGANISM: HIV-2

<400> SEQUENCE: 23
ctggtctgtt aggaccct                                                   18

<210> SEQ ID NO 24
<211> LENGTH: 18
<212> TYPE: DNA
<213> ORGANISM: HIV-2

<400> SEQUENCE: 24
tggtctgtta ggacccctt                                                  18

<210> SEQ ID NO 25
<211> LENGTH: 18
<212> TYPE: DNA
<213> ORGANISM: HIV-2

<400> SEQUENCE: 25
ggtctgttag gacccttc                                                   18

<210> SEQ ID NO 26
<211> LENGTH: 16
<212> TYPE: DNA
<213> ORGANISM: HIV-2

<400> SEQUENCE: 26
gtctgttagg accctt                                                     16

<210> SEQ ID NO 27
<211> LENGTH: 18
<212> TYPE: DNA
<213> ORGANISM: HIV-2

<400> SEQUENCE: 27
gtctgttagg acccttct                                                   18

<210> SEQ ID NO 28
<211> LENGTH: 27
<212> TYPE: DNA
<213> ORGANISM: HIV-2

<400> SEQUENCE: 28
aatttaatac gactcactat agggaga                                         27

<210> SEQ ID NO 29
<211> LENGTH: 33
<212> TYPE: DNA
<213> ORGANISM: HIV-2
```

-continued

```
<400> SEQUENCE: 29
gaaattaata cgactcacta tagggagacc aca                                  33

<210> SEQ ID NO 30
<211> LENGTH: 30
<212> TYPE: RNA
<213> ORGANISM: HIV-2

<400> SEQUENCE: 30
gaaggguccu aacagaccag ggucuuguua                                      30

<210> SEQ ID NO 31
<211> LENGTH: 53
<212> TYPE: DNA
<213> ORGANISM: HIV-2

<400> SEQUENCE: 31
ttcctgccgc ccttactgcc tttaaaaaaa aaaaaaaaa aaaaaaaaaa aaa             53

<210> SEQ ID NO 32
<211> LENGTH: 51
<212> TYPE: DNA
<213> ORGANISM: HIV-2

<400> SEQUENCE: 32
ttcctgccgc ccttactgtt taaaaaaaaa aaaaaaaaa aaaaaaaaaa a               51

<210> SEQ ID NO 33
<211> LENGTH: 16
<212> TYPE: DNA
<213> ORGANISM: HIV-2

<400> SEQUENCE: 33
aaagggtcct aacaga                                                     16

<210> SEQ ID NO 34
<211> LENGTH: 9
<212> TYPE: DNA
<213> ORGANISM: HIV-2

<400> SEQUENCE: 34 cgggcgcca                                                              9
```